(12) United States Patent
Fuso et al.

(10) Patent No.: US 6,566,468 B1
(45) Date of Patent: May 20, 2003

(54) NITROXYL DERIVATIVES WITH GLYCIDYL OR ALKYLCARBONYL GROUPS AS INITIATORS FOR RADICAL POLYMERIZATION

(75) Inventors: Francesco Fuso, Therwil (CH); Michael Roth, Lautertal (DE); Wiebke Wunderlich, Bickenbach (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/623,547
(22) PCT Filed: Feb. 26, 1999
(86) PCT No.: PCT/EP99/01233
§ 371 (c)(1), (2), (4) Date: Sep. 5, 2000
(87) PCT Pub. No.: WO99/46261
PCT Pub. Date: Sep. 16, 1999

(30) Foreign Application Priority Data

Mar. 9, 1998 (EP) .............................. 98810194

(51) Int. Cl.$^7$ ................................ C08F 4/00
(52) U.S. Cl. ................. 526/220; 526/217; 526/346; 526/329.2; 526/318.4; 526/335; 526/340.4; 526/303.1; 564/1
(58) Field of Search ......................... 526/217, 226, 526/346, 329.2, 318.4, 335, 340.4, 303.1; 564/1

(56) References Cited

U.S. PATENT DOCUMENTS 5,457,204 A 10/1995 Steinmann .................. 546/242
5,721,320 A 2/1998 Priddy et al. ............... 525/316

FOREIGN PATENT DOCUMENTS

| DE | 19949352 A1 * | 7/1984 |
| EP | 0135280 | 3/1985 |
| EP | 0155912 | 9/1985 |
| EP | 0634399 | 1/1995 |
| WO | 97/36894 | 10/1997 |
| WO | 97/36944 | 10/1997 |
| WO | 98/13392 | 4/1998 |

OTHER PUBLICATIONS

C. Hawker et al., Macromolecules, vol. 29, No. 16, (1996), pp. 5245–5254.
C. Hawker, TRIP, vol. 4, No. 6, (1996), pp. 183–188.
G. Moad et al., Macromolecules, vol. 28, (1995), pp. 8722–8728.
T. Connolly et al., Tetrahedron Letters, vol. 37, No. 28, (1996), pp. 4919–4922.
B. Howell et al., Polymer Bulletin, vol. 37, (1996), pp. 451–456.
I. Li et al., Macomolecules, vol. 28, (1995), pp. 6692–6693.
S. Kobatake et al., Macromolecules, vol. 30, (1997), pp. 4238–4240.
E. Malmström et al., Tetrahedron, vol. 53, No. 45, (1997), pp. 15225–15236.

* cited by examiner

Primary Examiner—David W. Wu
Assistant Examiner—William K Cheung
(74) Attorney, Agent, or Firm—Tyler A. Stevenson

(57) ABSTRACT

Glycidyl and alkylcarbonyl functional nitroxide radical polymerization initiator compounds of formula (Ia) or (Ib),

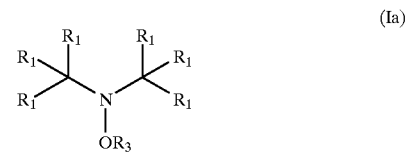

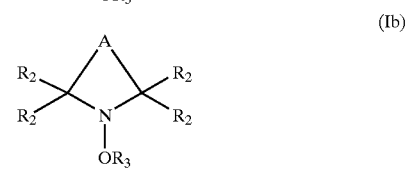

where $R_1$, $R_2$ and A are as defined within,
$R_3$ is a radical of formula (II)

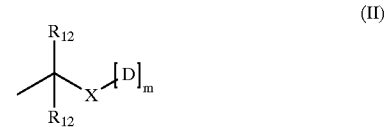

where
X is phenylene, naphthylene or biphenylene, which are unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;
the $R_{12}$ are independently of each other H or $CH_3$;
D is a group

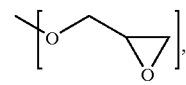

a group C(O)—$R_{13}$ or a group C(O)—$R_9$—C(O)—$R_{13}$;
$R_{13}$ is $C_1$–$C_{18}$alkyl and
m is a number from 1 to 4, provide polymeric resin products having low polydispersity, polymerization processes that proceed with good monomer to polymer conversion efficiencies and polymers that contain a glycidyl or alkylcarbonyl group.

13 Claims, No Drawings

NITROXYL DERIVATIVES WITH GLYCIDYL OR ALKYLCARBONYL GROUPS AS INITIATORS FOR RADICAL POLYMERIZATION

The present invention relates to glycidyl or alkylcarbonyl functional nitroxyle derivatives, a polymerizable composition comprising a) at least one ethylenically unsaturated monomer and b) a glycidyl or alkylcarbonyl functional nitroxide initiator compound. Further aspects of the present invention are a process for polymerizing ethylenically unsaturated monomers, the use of glycidyl or alkylcarbonyl functional nitroxide initiators for radical polymerization.

More specifically, in one of its aspects the present invention relates to polymerizable compositions and polymerization processes which provide polymeric resin products having low polydispersity, which polymerization processes proceed with good monomer to polymer conversion efficiencies. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions. The polymers produced by the present invention contain a glycidyl or alkylcarbonyl group attached to the starting molecule of the radical chain reaction.

Polymers or copolymers prepared by free radical polymerization processes inherently have broad molecular weight distributions or polydispersities which are generally higher than about four. One reason for this is that most of the free radical initiators have half lives that are relatively long, ranging from several minutes to many hours, and thus the polymeric chains are not all initiated at the same time and the initiators provide growing chains of various lengths at any time during the polymerization process. Another reason is that the propagating chains in a free radical process can react with each other in processes known as combination and disproportionation, both of which are irreversibly chain-terminating reaction processes. In doing so, chains of varying lengths are terminated at different times during the reaction process, resulting in resins consisting of polymeric chains which vary widely in length from very small to very large and which thus have broad polydispersities. If a free radical polymerization process is to be used for producing narrow molecular weight distributions, then all polymer chains must be initiated at about the same time and termination of the growing polymer-chains by combination or disproportionation processes must be avoided.

Conventional radical polymerization reaction processes pose various significant problems, such as difficulties in predicting or controlling the molecular weight, the polydispersity and the modality of the polymers produced. These prior art polymerization processes produce polymers having broad polydispersities and in some instances, low polymerization rates. Furthermore, free radical polymerization processes in bulk of the prior art are difficult to control because the polymerization reaction is strongly exothermic and an efficient heat removal in the highly viscous polymer is mostly impossible. The exothermic nature of the prior art free radical polymerization processes often severely restricts the concentration of reactants or the reactor size upon scale-up. In case that additional functional groups, such as glycidyl groups are present in one of the monomers, these may be transformed into undesired groups under such reaction conditions.

Due to the above mentioned uncontrollable polymerization reactions, gel formation in conventional free radical polymerization processes are also possible and cause broad molecular weight distributions and/or difficulties during filtering, drying and manipulating the product resin.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned R'R"N—O. radical groups are derived from tetraethylisoindoline, tetrapropylisoindoline, tetramethylpiperidine, tetramethylpyrrolidine or di-t-butylamine.

The radical initiators, polymerization processes and resin products of the present invention have an additional glycidyl or alkylcarbonyl group, which can be used for further reactions. The resulting resins are useful in many applications.

The glycidyl or alkylcarbonyl group of the present initiators remainsessentially unchanged during the radical polymerization reaction. Therefore the radical initiators of the present invention offer the possibility, after the radical polymerizabon is accomplished or stopped, to react the glycidyl group of the oligomers or polymers in a second step with nucleophiles such as alcohols, mercaptanes, amines, metal organic compounds or the like, thereby changing the properties of the oligomers or polymers.

The glycidyl group of the initiators can also be reacted in a first step for example by anionic polymerization in the presence of for example dicyandiamide, butyl-Lithium or other strong bases leading to oligomeric/polymeric radical initiators.

S. Kobatake et al, Macromolecules 1997, 30, 4238–4242 and in WO 97/36894 disclose the anionic polymerization of butadiene in the presence of compound (a) which contains a glycidyl group in a side chain. This compound acts as a terminating reagent for the anionic polymerization of butadiene.

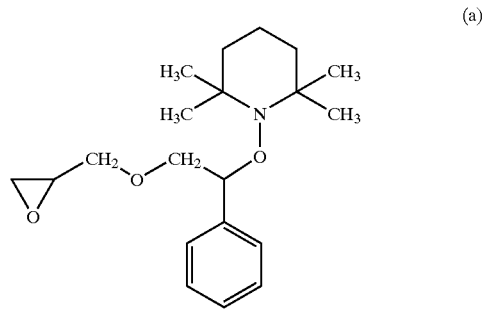

(a)

The resulting macromolecule can be further used as a macroinitiator for radical polymerization and for preparing block copolymers containing a poylbutadiene segment.

The present invention provides initiators for radical polymerization which contain the glycidyl or alkylcarbonyl group attached directly or separated by a spacer group to the aryl group. The initiators show a high reactivity, good rates of polymerization and good monomer to polymer conversions.

The remaining glycidyl or alkylcarbonyl group is highly reactive towards nucleophiles and can readily be transformed into other chemical groups i desired.

The compounds of the present invention are also useful as terminating agents in the anionic polymerization of for example butadiene as described in WO 97l36894.

The polymerization processes and resin products of the present invention are useful in many applications, including a variety of specialty applications, such as for the preparation of block copolymers which are useful as compatibilizing agents for polymer blends or dispersing agents for coating systems or for the preparation of narrow molecular weight resins or oligomers for use in coating technologies and thermoplastic films or as toner resins and liquid immersion development ink resins or ink additives used for electrophotographic imaging processes.

Surprisingly, it has been found that it is possible to produce polymers or copolymers of narrow polydispersity and a high monomer to polymer conversion even at relative low temperatures and at short reaction times, leaving the glycidyl group essentially unchanged. The resulting polymers/copolymers are of high purity and in many cases colorless, therefore not requiring any further purification.

One subject of the present invention is to provide new initiators of formula (Ia) or (Ib)

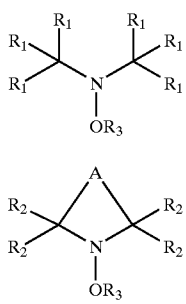

wherein the $R_1$, are each independently of one another hydrogen, halogen, $NO_2$, cyano,
- $-CONR_5R_6$, $-(R_9)COOR_4$, $-C(O)-R_7$, $-OR_8$, $-SR_8$, $-NHR_8$, $-N(R_8)_2$, carbamoyl, di($C_1-C_{18}$alkyl)carbamoyl,
- $-C(=NR_5)(NHR_6)$; unsubstituted $C_1-C_{18}$alkyl, $C_2-C_{18}$alkenyl, $C_2-C_{18}$alkynyl, $C_7-C_9$phenylalkyl, $C_3-C_{12}$cycloalkyl or
- $C_2-C_{12}$heterocycloalkyl; or
- $C_1-C_{18}$alkyl, $C_2-C_{18}$alkenyl, $C_2-C_{18}$ alkynyl, $C_7-C_9$phenylalkyl, $C_3-C_{12}$cycloalkyl or $C_2-C_{12}$heterocycloalkyl, which are substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino; or phenyl, naphthyl, which are unsubstituted or substituted by $C_1-C_4$alkyl, $C_1-C_4$alkoxy, $C_1-C_4$alkylthio, halogen, cyano, hydroxy, carboxy, $C_1-C_4$alkylamino or di($C_1-C_4$alkyl) amino;
- $R_4$ is hydrogen, $C_1-C_{18}$alkyl, phenyl, an alkali metal cation or a tetraalkylammonium cation;
- $R_5$ and $R_6$ are hydrogen, $C_1-C_{18}$alkyl, $C_2-C_{18}$alkyl which is substituted by at least one hydroxy group or, taken together, form a $C_2-C_{12}$alkylene bridge or a $C_2-C_{12}$-alkylene bridge interrupted by at least one O or/and $NR_8$ atom;
- $R_7$ is hydrogen, $C_1-C_{18}$alkyl or phenyl;
- $R_8$ is hydrogen, $C_1-C_{18}$alkyl or $C_2-C_{18}$alkyl which is substituted by at least one hydroxy group;
- $R_9$ is $C_1-C_{12}$alkylene or a direct bond;
- or all $R_1$ form together the residue of a polycyclic cycloaliphatic ring system or a polycyclic heterocloaliphatic ring system with at least one di- or trivalent nitrogen atom;
- the $R_2$ are independently of each other phenyl or $C_1-C_6$alkyl or two together with the linking carbon atom form a $C_5-C_6$cycloalkyl group;
- A is a divalent group required to form a cyclic 5-, 6- or 7-membered ring and
- $R_3$ is a radical of formula (II)

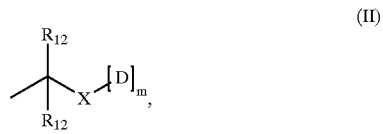

wherein
X is phenylene, naphthylene or biphenylene, which are unsubstituted or substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino; the $R_{12}$ are independently of each other H or $CH_3$;

D is a group

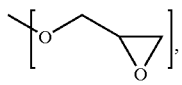

a group $C(O)-R_{13}$ or a group $C(O)-R_9-C(O)-R_{13}$;
$R_{13}$ is $C_1-C_{18}$alkyl and
m is a number from 1 to 4.

Halogen is fluoro, chloro, bromo or iodo.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

The alkenyl radicals in the various substituents may be linear or branched. Examples of $C_2-C_{18}$ alkenyl are vinyl, allyl, 2-methylallyl, butenyl, hexenyl, undecenyl and octadecenyl. Preferred alkenyls are those, wherein the carbon atom in the 1-position is saturated and where the double bond is not activated by substituents like O, C=O, and the like.

Examples of $C_2-C_{18}$alkynyl are ethynyl,2-butynyl, 3hexynyl, 5-undecynyl, 6-octadecynyl. The alkynyl radicals may be linear or branched.

$C_7-C_9$phenylalkyl is for example benzyl, phenylpropyl, α,α-dimethylbenzyl or α-methylbenzyl.

$C_3-C_{12}$cycloalkyl which is unsubstituted or substituted by 1, 2 or 3 $C_1-C_4$alkyl is typically cyclopropyl, cyclopentyl, methylcyclopentyl, dimethylcyclopentyl, cyclohexyl, methylcyclohexyl.

Alkyl substituted by —OH is typically 2-hydroxyethyl, 2-hydroxypropyl or 2-hydroxybutyl. $C_1-C_{18}$Alkyl substituted by $C_1-C_8$alkoxy, preferably by $C_1-C_4$alkoxy, in particular by methoxy or ethoxy, is typically 2-methoxyethyl, 2-ethoxyethyl, 3-methoxypropyl, 3-ethoxypropyl, 3-butoxypropyl, 3-octoxypropyl and 4-methoxybutyl.

$C_1-C_{18}$Alkyl substituted by di($C_1-C_4$alkyl)amino is preferably e.g. dimethylamino, diethylamino, 2dimethylaminoethyl, 2-diethylaminoethyl, 3-dimethylaminopropyl, 3-diethylaminopropyl, 3-dibutylaminopropyl and 4-diethylaminobutyl.

$C_1$–$C_{18}$Alkyl substituted by $C_1$–$C_4$alkylamino is preferably e.g. methylamino, ethylamino, 2-methylaminoethyl, 2-ethylaminoethyl, 3-methylaminopropyl, 3-ethylaminopropyl, 3-buty-aminopropyl and 4-ethylaminobutyl.

$C_1$–$C_8$Alkoxy and, preferably $C_1$–$C_4$alkoxy, are typically methoxy, ethoxy, propoxy, isopropoxy, butoxy, isobutoxy, pentoxy, isopentoxy, hexoxy, heptoxy or octoxy.

$C_1$–$C_4$Alkylthio is typically thiomethyl, thioethyl, thiopropyl, thioisopropyl, thiobutyl and thioisobutyl.

$C_2$–$C_{12}$heterocycloalkyl is typically oxirane, 1,4-dioxane, tetrahydrofuran, γbutyrolactone, ε-caprolactam, oxirane, aziridine, diaziridine, pyrrole, pyrrolidine, thiophen, furan, pyrazole, imidazole, oxazole, oxazolidine, thiazole, pyran, thiopyran, piperidine or morpholine.

Examples of $C_2$–$C_{12}$alkylene bridges, preferably of $C_2$–$C_6$alkylene bridges, are ethylene, propylene, butylene, pentylene, hexylene.

$C_2$–$C_{12}$alkylene bridges interrupted by at least one N or O atom are, for example, —CH$_2$—O—CH$_2$—CH$_2$—, —CH$_2$—O—CH$_2$—CH$_2$—CH$_2$—, —CH$_2$—O—CH$_2$—CH$_2$—CH$_2$— CH$_2$—CH$_2$—O—CH$_2$—CH$_2$—O—CH$_2$—, —CH$_2$—NH—CH$_2$—CH$_2$—, —CH$_2$—NH—CH$_2$—CH$_2$—CH$_2$—, —CH$_2$—NH—CH$_2$—CH$_2$—CH$_2$—CH$_2$—, —CH$_2$—NH—CH$_2$—CH$_2$—NH—CH$_2$— or —CH$_2$—NH—CH$_2$—CH$_2$—O—CH$_2$—.

Phenyl substituted by 1, 2 or 3 $C_1$–$C_4$alkyl or $C_1$–$C_4$alkoxy is typically methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of polycyclic cycloaliphatic ring systems are adamantane, cubane, twistane, norbornane, bicyclo[2.2.2]octane or bicyclo[3.2.1]octane.

An example of a polycyclic heterocycloaliphatic ring system is hexamethylentetramine (urotropine).

Examples for a divalent group A required to form a cyclic 5-, 6- or 7-membered ring are: $C_2$–$C_4$alkylene, $C_2$–$C_4$alkenylene, $C_2$–$C_4$alkinylene, 1,2 phenylene which groups may be unsubstituted or substituted by NO$_2$, halogen, amino, hydroxy, cyano, carboxy, carbonyl, $C_1$–$C_{18}$ alkoxy, $C_1$–$C_{18}$ acyloxy, benzoyloxy, $C_1$–$C_{18}$alkylthio, $C_1$–$C_{18}$alkylamino or di($C_1$–$C_{18}$alkyl)amino or phenyl.

When A has the meaning of $C_2$–$C_4$alkylene or $C_2$–$C_4$alkenylene, these groups may also be interrupted by an O or N atom.

$C_2$–$C_4$alkylene bridges interrupted by at least one N or O atom are, for example, —CH$_2$—O—CH$_2$—CH$_2$—, —CH$_2$—O—CH$_2$—, —O—CH$_2$—CH$_2$—,—O—CH$_2$—O—CH$_2$—, —CH$_2$CH$_2$—CH$_2$—, —NH—CH$_2$—, —CH$_2$—, —NH—CH$_2$—NH—CH$_2$—, —O—CH$_2$— or —CH$_2$—O—C(O)—.

The C-atom to which the substituents $R_1$ are bound is preferably a secondary or tertiary C-atom more preferably it is a tertiary C-atom.

Preferred is a compound of formula (Ia) or (Ib), wherein the $R_1$ are each independently of one another NO$_2$, cyano, —($R_9$)COOR$_4$, —CONR$_5$R$_6$, —C(O)—R$_7$, —OR$_8$, carbamoyl, di($C_1$–$C_{18}$alkyl)carbamoyl, —C(=NR$_5$)(NHR$_6$);
unsubstituted $C_1$–$C_8$alkyl or $C_5$–$C_7$cycloalkyl;
or phenyl, which is unsubstituted or substituted by $C_1$–$C_4$alkyl, $C_1$–$C_4$alkoxy, cyano, hydroxy, carboxy, $C_1$–$C_4$alkylamino or di($C_1$–$C_4$alkyl)amino;
$R_4$ is $C_1$–$C_8$alkyl, phenyl, an alkali metal cation or a tetraalkylammonium cation;
$R_5$ and $R_6$ are hydrogen, $C_1$–$C_8$alkyl, $C_2$–$C_8$alkyl which is substituted by at least one hydroxy group or, taken together, form a $C_2$–$C_6$alkylene bridge;

$R_7$ is, $C_1$–$C_8$alkyl or phenyl;
$R_8$ is $C_1$–$C_8$alkyl or $C_2$–$C_8$alkyl which is substituted by at least one hydroxy group;
$R_9$ is $C_1$–$C_4$alkylene or a direct bond;
the $R_2$ are independently $C_1$–$C_6$alkyl;
A is a divalent group required to form a cyclic 5-, 6- or 7-membered ring and
$R_3$ is a radical of formula (II)

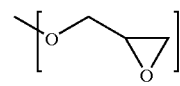

(II)

wherein
X is phenylene, naphthylene or biphenylene, which are unsubstituted or substituted by NO$_2$, halogen, amino or hydroxy;
the $R_{12}$ are independently of each other H or CH$_3$;
D is a group

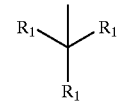

or a group C(O)—$R_{13}$;
$R_{13}$ is $C_1$–$C_4$alkyl and
m is a number from 1 to 4.

More preferred is a compound of formula (Ia) or (Ib), wherein the group

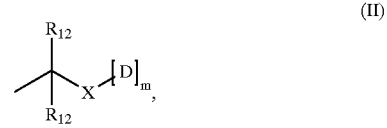

is

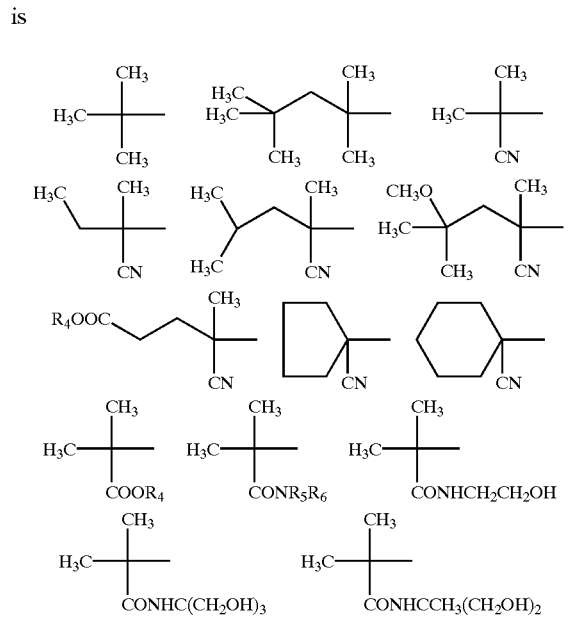

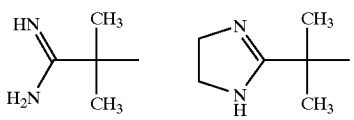

the $R_2$ are independently $C_1$–$C_6$alkyl;

A is a divalent group required to form a cyclic 5-, 6- or 7-membered ring and $R_3$ is a radical of formula (II)

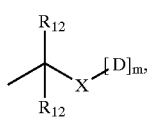

(II)

wherein

X is phenylene, naphthylene or biphenylene;

one $R_{12}$ is H and the other $R_{12}$ is $CH_3$;

D is a group

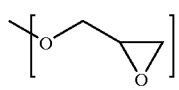

or a group C(O)—$R_{13}$;

$R_{13}$ is $CH_3$ and m is a number from 1 to 2.

Particularly preferred is a compound of formula (Ib), wherein the $R_2$ are independently $CH_3$ or $C_2H_5$;

A is a divalent group required to form a cyclic 5-or 6-membered ring and $R_3$ is a radical of formula (II)

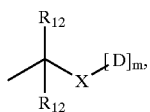

(II)

wherein

X is phenylene, naphthylene or biphenylene;

one $R_{12}$ is H and the other $R_{12}$ is $CH_3$;

D is a group

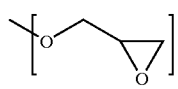

or a group C(O)—$R_{13}$;

$R_{13}$ is $CH_3$ and m is a number from 1 to 2.

Most preferred is a compound of formula (III)

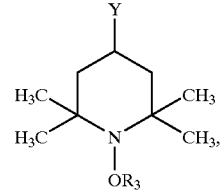

(III)

wherein $R_3$ has the meaning as defined above;

Y is H, $OR_{10}$, $NR_{10}R_{11}$, —O—C(O)—$R_{10}$ or $NR_{11}$—C(O)—$R_{10}$;

$R_{10}$ and $R_{11}$ independently are hydrogen, phenyl, $C_1$–$C_{18}$alkyl, $C_2$–$C_{18}$alkenyl, $C_2$–$C_{18}$alkinyl or $C_2$–$C_{18}$alkyl which is substituted by at least one hydroxy group or, if Y is $NR_{10}R11$, taken together, form a $C_2$–$C_{12}$alkylene bridge or, a $C_2$–$C_{12}$alkylene bridge interrupted by at least one O atom.

Amongst the most preferred compounds those are of particular use, wherein $R_3$ is

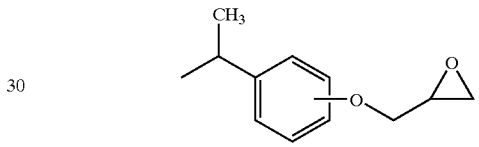

or

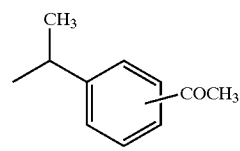

Y is H, $OR_{10}$, $NR_{10}R_{11}$, —O—C(O)—$R_{10}$ or $NR_{11}$—C(O)—$R_{10}$;

$R_{10}$ and $R_{11}$ are independently hydrogen or $C_1$–$C_6$alkyl.

A further subject of the present invention is a polymerizable composition, comprising a) at least one ethylenically unsaturated monomer or oligomer, and b) an initiator compound of formula (Ia) or (Ib).

Suitable initiator compounds and examples for the different groups and substituents A, Y, X and $R_1$ to $R_{11}$ are already mentioned including their preferences.

Typically the amount of the initiator compound of formula (Ia) or (Ib) is in the range of 0.01 mol-% to 30 mol-% based on the monomer, oligomer or monomer/oligomer mixture used.

If monomer mixtures are used the average molecular weight is taken for calculating mol-%.

The initiator compound of formula (Ia) or (Ib) is preferably present in an amount of 0.01 mol-% to 10 mol-%, more preferably in an amount of 0.05 mol-% to 5 mol-%, based on the monomer, oligomer or monomer/oligomer mixture used.

The monomers suitable for use in the present invention may be water-soluble or water-insoluble. Water soluble monomers contain typically a salt of a carboxylic acid group. Water insoluble monomers are typically free of acid and phenolic groups. Typical metal atoms are Na, K or Li.

Typical monoethylenically unsaturated monomers free of carboxylic acid and phenolic groups which are suitable for this invention include the alkyl esters of acrylic or methacrylic acids such as methyl acrylate, ethyl acrylate, butyl acrylate, methyl methacrylate, ethyl methacrylate, butyl methacrylate and isobutyl methacrylate; the hydroxyalkyl esters of acrylic or methacrylic acids, such as hydroxyethyl acrylate, hydroxypropyl acrylate, hydroxyethyl methacrylate, and hydroxypropyl methacrylate; acrylamide, methacrylamide, N-tertiary butylacrylamide, N-methylacrylamide, N,N-dimethylacrylamide; acrylonitrile, methacrylo nitrile, allyl alcohol, dimethylaminoethyl acrylate, dimethylaminoethyl methacrylate, phosphoethyl methacrylate, N-vinylpyrrolidone, N-vinylformamide, N-vinylimidazole, vinyl acetate, conjugated dienes such as butadiene or isoprene, styrene, styrenesulfonic acid salts, vinylsulfonic acid salts and 2-acrylamido-2-methylpropane-sulfonic acid salts and acryloil chloride.

Preferred ethylenically unsaturated monomers or oligomers are selected from the group consisting of styrene, substituted styrene, conjugated dienes, acrolein, vinyl acetate, (alkyl)acrylic acidanhydrides, (alkyl)acrylic acid salts, (alkyl)acrylic esters or (alkyl)acrylamides.

Particularly preferred ethylenically unsaturated monomers are styrene, α-methyl styrene, p-methyl styrene or butadiene.

In a most preferred composition the ethylenically unsaturated monomer is styrene.

Preferred acrylates are methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, acrylonitrile, acrylamide or methacrylamide.

Examples for $C_8$–$C_{16}$ ethylenically unsaturated phenolics, which may also be used as comonomers include 4-hydroxy styrene, 4-hydroxy, α-methyl styrene, and 2,6-ditert. butyl, 4-vinyl phenol.

Another class of carboxylic acid monomers suitable for use as comonomers in this invention are the alkali metal and ammonium salts of $C_4$–$C_6$-ethylenically unsaturated dicarboxylic acids. Suitable examples include maleic acid, maleic anhydride, itaconic acid, mesaconic acid, fumaric acid and citraconic acid. Maleic anhydride (and itaconic acid are) is the preferred monoethylenically unsaturated dicaiboxylic acid monomer(s).

The acid monomers suitable for use in this invention are in the form of the alkali metal salts or ammonium salts of the acid. The polymerizable composition of the present invention may additionally comprise a solvent selected from the group consisting of water, alcohols, esters, ethers, ketones, amides, sulfoxides, hydrocarbons and halogenated hydrocarbons.

The invention also relates to a free radical polymerization process and polymers obtained thereby, which process overcomes many of the problems and disadvantages of the afore mentioned prior art processes.

Therefore another subject of the present invention is a process for preparing an oligomer, a cooligomer, a polymer or a copolymer (block or random) by free radical polymerization of at least one ethylenically unsaturated monomer/ oligomer, which comprises (co)polymerizing the monomer or monomers/oligomers in the presence of an initiator compound of formula (Ia) or (Ib) under reaction conditions capable of effecting scission of the O—$R_3$ (O—C) bond to form two free radicals, the radical .$R_3$ being capable of initiating polymerizabon.

Preferably the process is carried out in such a way that the scission of the O—C bond is effected by, heating ultrasonic treatment or exposure to electromagnetic radiation, ranging from γ to microwaves.

More preferred the scission of the O—C bond is effected by heating and takes place at a temperature of between 50° C. and 180° C.

Preferred initiators and ethylenically unsaturated monomers have already been mentioned above.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

When monomer mixtures or monomerloligomer mixtures are used, the calculation of mol-% is based on an average molecular weight of the mixture.

Hydrophilic monomers, polymers and copolymers of the present invention can be separated from one another or from the polymerization reaction mixture by, for example, changing the pH of the reaction media and by other well known conventional separation techniques.

The polymerization temperature may range from about 50° C. to about 180° C., preferably from about 80° C. to about 150° C. At temperatures above about 180° C., the controlled conversion of the monomer into polymer decreases, and uncertain and undesirable by-products like thermally initiated polymer are formed or destruction of the polymerization regulator may occur. Frequently, these by-products discolor the polymer mixture and a purification step may be required to remove them, or they may be intractable.

Therefore the surprisingly high reactivity of the present initiators which are already active at relatively low temperatures leads to short reaction times. The resulting polymers are usually colourless and they can be used in most cases without any further purification step. This is an Important advantage when industrial scale-up is considered.

After the polymerizing step is complete, the formed (co)polymer obtained is isolated. The isolating step of the present process is conducted by known procedures, e.g. by distilling off the unreacted monomer or by precipitation in a suitable nonsolvent, filtering the precipitated polymer followed by washing and drying the polymer.

Another preferred process is for preparing a block copolymer involving at least two stages, which comprises forming a polymer with alkoxyamine end groups of the general structure of formula (IVa) or (IVb)

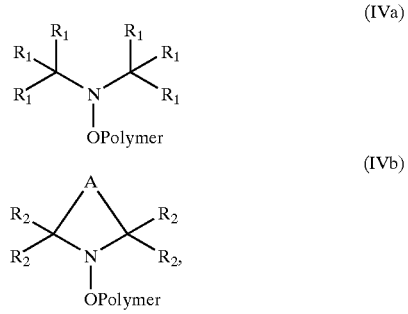

wherein $R_1$, $R_2$ and A are as defined above including the preferences, the polymer containing the initiator group —$R_3$ and having the oxyamine group essentially attached as terminal group, and adding a further monomer followed by heating to form a block copolymer by radical initiated polymerization.

Suitable monomers and comonomers are already mentioned.

The polymer of formula (IVa) or (IVb) may be isolated prior to the next reaction step or it may be used without isolation, and the second monomer is added to the reaction mixture of the first step.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 gmol, preferably from 2 000 to 250 000 gmol and, more preferably, from 2 000 to 200 000 gmol. When produced in bulk, the number average molecular weight may be up to 500 000 (with the same minimum weights as mentioned above). The number average molecular weight may be determined by size exclusion chromatography (SEC), gel permeation chromatography (GPC), matrix assisted laser desorptlonfionization mass spectrometry (MALDI-MS) or, If the initiator carries a group which can be easily distinguished from the monomer(s), by NMR spectroscopy or other conventional methods.

Thus, the present invention also encompasses in the synthesis novel block, multi-block, star, gradient, random, hyperbranched and dendritic copolymers, as well as graft or copolymers.

The polymers prepared by the present invention are useful for example in following applications:

adhesives, detergents, dispersants, emulsifiers, surfactants, defoamers, adhesion promoters, corrosion inhibitors, viscosity improvers, lubricants, rheology modifiers, impact modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers. Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly (meth)-acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623–1627, dendrimers as described by K. Matyaszewski et al. in Macromolecules 1996, Vol 29, No. 12, pages 4167–4171, graft (co) polymers as described by C. J. Hawker et al. in Macromol. Chem. Phys. 198, 155–166(1997), random copolymers as described by C. J. Hawker In Macromolecules 1996, 29, 2686–2688, or diblock and triblock copolymers as described by N. A. Listigovers in Macromolecules 1996, 29, 8992–8993.

A further subject of the present invention is a polymer or oligomer, containing at least one initiator group —$R_3$ and at least one oxyamine group of formula

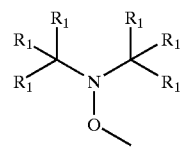

or

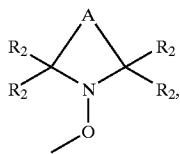

wherein A, R$_1$ and R$_2$ are as defined above, obtainable by the process defined above.

Still another object of the present invention is the use of a compound of formula (Ia) or (Ib) as defined above, including the preferences, for polymerizing ethylenically unsaturated monomers.

The compounds of formula (Ia) or (Ib) may also be useful for terminating the anionic polymerization of butadiene. A process for the preparation of such nitroxyl terminated diene rubbers and suitable vinyl aromatic monomers are for example disclosed in WO 97/36894.

The nitroxyl terminated diene rubbers produced using the compounds of formula (Ia) or (Ib), preferably those of formula (Ib), will have at least one nitroxyl group attached to a chain-end. Typically, the diene monomer is polymerized under anionic polymerization conditions and terminated in the presence of the nitroxyl containing compound. Preferably the diene monomer is a 1,3-conjugated diene such as butadiene, isoprene or chloroprene. At temperatures above approximately 60° C., the nitroxyl containing macrocompound activates to form a stable free radical. If activation occurs in the presence of vinyl aromatic monomers, such as styrene, a vinyl aromatic polymer segment is formed. These rubber modified styrene polymers lead for example to high impact styrene (HIPS), impact polystyrene(IPS) or acryl-butadiene-styrene rubbers (ABS).

The compounds of the present invention may be prepared in different ways according to known methods. These methods are for example described in Macromol. Rapid Commun. 17, 149,1996, Macromol Symp. 111, 47, (1996), Polym. Degr. Stab. 55, 323 (1997), Synlett 1996, 330, U.S. Pat. No. 5,498,679 or U.S. Pat. No. 4,921,962.

The method of reacting the nitroxyl with the corresponding ethylene glycidylether in the presence of tert. butyl hydroperoxide as described in U.S. Pat. No. 4,921,962 is a preferred method. As described in Tetrahedron Lett 37, 4919, 1996 the reaction may also be carried out photochemically in the presence of di-tert. butyl peroxide.

The starting compounds, which are phenylglycidylethers are known and either commercially available or may be prepared according to EP 226543.

The following examples illustrate the invention.

A) Preparation of Compounds

Example A1

2,2,6,6-Tetramethyl-1-(1-(4-oxiranylmethoxy-phenyl)-ethoxy)-4-propoxy-piperidine (101)

A: A 70% aqueous solution of terL-butylhydroperoxyde (26,4 g) is extractively dehydrated in two portions with each of 25 g 2-(4-ethyl-phenoxymethyl)-oxirane. The organic extracts are combined, a molecular sieve is added and the mixture is stored under argon atmosphere.

B: A mixture of 2-(ethyl-phenoxymethyl)-oxirane (57 g), 4-propoxy-2,2,6,6-tetramethylpiperidine-1-oxyl (10,7 g) and molybdenum(VI)oxide (0,72 g) are purged with Argon for one hour. The mixture is then heated up to 70° C. and the solution prepared under A) is added under stirring within 30 minutes. Pressure is reduced to 200 mbar and the mixture is heated for 18 hours at 100° C. After the reaction is completed the mixture is cooled to room temperature and the pressure is allowed to raise to normal pressure. Ethylacetate and water is added. The water phase is separated and extracted once with ethylacetate. The organic phases are combined, washed with a 10% solution of sodium ascorbate and in a second step with water, dried over sodium sulfate and concentrated. Excessive amounts of 2-(4ethyl-phenoxymethyl)-oxirane are removed at 80° C./0,01 mbar. The raw product is subsequently chromatographically purified on silica with petrolether/ethylacetate =7/1 as eluent. A clear colorless oil is obtained, corresponding to the compound of formula (101)

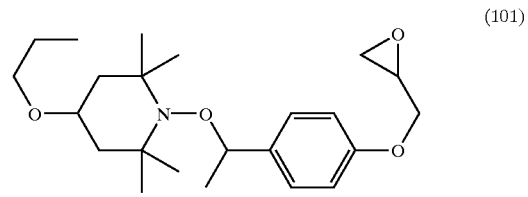

(101)

Elemental Analysis: calculated C$_{23}$H$_{37}$NO$_4$: 70,55% C; 9,52% H; 3,57% N. found: 70,66% C; 9,60% H; 3,43% N.

Example A2

2,2,6,6-Tetramethyl-1-[1-(2-oxiranylmethoxy-phenyl)-ethoxyl-]4-propoxy-piperidine (102)

A: To 18 g of a 70% aqueous solution of tert.-butylhydroperoxide is added 9,9 g of 2-(2-ethyl-phenoxymethyl)-oxirane and 4 g of 4-propoxy-2,2,6,6-tetramethylpiperidine-1-oxyl. Water is separeted and the organic phase dried over molecular sieve.

B: To a mixture of 4-propoxy-2,2,6,6-tetramethylpiperidine-1-oxyl (6 g) and 2-(2-ethyl-phenoxymethyl)-oxirane (40 g) molybdenum(VI)oxyde (0,13 g) is added. The pressure is then reduced to about 500 mbar and the mixture heated to 80° C. The solution prepared under A) is then added under stirring within ¾ h. Stirring is continued for another 16 h at 80° C./500 mbar. The reaction mixture is then cooled to room temperature and the pressure is allowed to raise to normal pressure. Ethylacetate and an aqueous solution of ascorbinic acid (20%) are added and the mixture stirred for another hour. The water phase is separated off, the organic phase washed three times with water and dried over sodium sulfate. After filtration and evaporating off the solvent excessive 2-(2-ethyl-phenoxymethyl)-oxirane is distilled off (0,08 mbar/70° C.). The residue is purified by column chromatography on silica gel with petrolether/ethylacetate=9:1 as the eluent. The product corresponding to formula

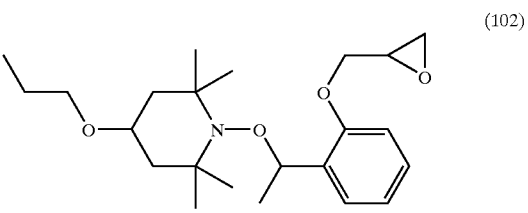

(102)

is obtained as a resin.

$^1$H-NMR (300 MHz): 0.7–2.0 (m, 24H); 2.7–2.85 (m, 1H); 2.85–3.0 (m, 1H); 3.3–3.6 (m 4H); 3.9–4.1 (m, 1H); 4.15–4.25 (m, 1H); 5.2 (q, 1H); 6.75–7.5 (aromatic H, 4H).

Example A3

N,N-Di-tert.-butyl- O-[1-(4-Oxiranylmethoxy-phenyl)-ethyl]-hydroxylamine

A: A 70% aqueous solution of tert.-butylhydroperoxide (5.35 g) is extracted with two portions with each of 5 g 2-(4ethyl-phenoxymethyl)-oxirane. The organic extracts are combined and dried over molecular sieve.

B: To a mixture of di-tert.-butylnitroxyl (2,2 g) and 2-(4ethyl-phenoxymethyl)-oxirane (9,7 g) molybdenum(VI) oxyde (0,14 g) is added. The pressure is then reduced to about 500 mbar and the mixture heated to 80° C. The solution prepared under A) is then added under stirring within 1,5 h. Stirring is continued for another 16 h at 80° C./500 mbar. The reaction mixture is cooled to room temperature and the pressure is allowed to raise to normal pressure. After dilution wit ethylacetate the mixture is filtered through a short column of alumina. The ethyl acetate solvent is evaporated and the residue distilled in a Kugelrohr oven (0,08 mbar/100° C.) to remove excessive amounts of 2-(4-ethyl-phenoxymethyl)-oxirane. After column chromatography on silica gel with petrolether/ethylacetate =9:1 as the eluent, the product corresponding to formula (103)

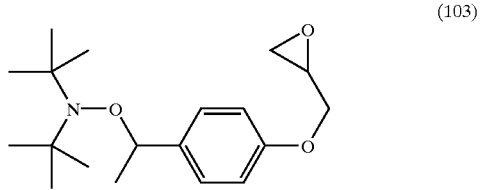

(103)

is obtained as a resin.

$^1$H-NMR (300 MHz): 1.0 (s, 9H); 1.3 (s, 9H); 1.46 (d, 3H); 2.73–2.77 (m, 1H);288–292 (m, 1H); 3.32–3.38 (m, 1H); 3.92–4.01 (m, 1H); 4.16–4.22 (m, 1H); 4.77 (q, 1H); 6.84+7.23 (AA'BB'-system, 2×2H).

Example A4

Preparation of 1{-(4-[1-(2,2,6,6-Tetramethyl-piperidin-1-yloxy)-ethyl]-phenyl}-ethanone A: A 70% aqueous solution of tert.-butylhydroperoxyde (26.4 g) is extractively dehydrated in two portions with each of 30 g 4-ethylacetophenone. The organic extracts are combined, a molecular sieve is added and the mixture is stored under argon atmosphere.

B:,A mixture of 4-ethylacetophenone (23 g), 2,2,6,6-tetramethylpiperidine-1-oxyl (10,7 g) and molybdenum(VI) oxide (0,67 g) are purged with Argon for one hour. The mixture is then heated up to 70° C. and the solution prepared under A) is added drop wise under stirring within 5 minutes. Pressure is reduced to 300 mbar and the mixture is heated for 18 hours at 70° C. After the+reaction is completed the mixture is cooled to room temperature and the pressure is allowed to raise to normal pressure. Ethylacetate and water is added. The water phase is separated and extracted three times with ethylacetate. The organic phases are combined, washed with water, dried over Magnesium sulfate and concentrated. Excessive amounts of 2-(4-ethyl-phenoxymethyl)-oxirane are removed at 40° C./0,2 mbar. The raw product is subsequently chromatographically purified on silica with petrolether/ethylacetate=95/5 as eluent. A white+powder is obtained after recrystalization from pentane, corresponding to the compound of formula (104), having a melting point of 61.5–63° C.

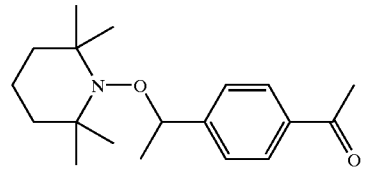

(104)

Elemental Analysis: calculated $C_{19}H_{29}NO_2$ 75.21% C, 9.63% H, 4.61% N; found 75.09% C, 9.46% H, 4.37% N.

The examples given in table 1 are prepared in analogy to example A1 and A2.

TABLE 1

| Example No. | Formula | Data |
|---|---|---|
| A5 | ![(105)] | $^1$H-NMR: (in ppm, 300 MHz) 0.5–1.7(m, 18H,); 1.45(d, 3H); 2.7–2.76 (m, 1H); 2.83–2.93(m, 1H); 3.28–3.4(m, 1H); 3.89–3.96(m, 1H); 4.14–4.2(m, 1H); 4.73(q, 1H); 6.85+7.23(aromatic H, 2x2H) |
| A6 | ![(106)] | 0.5–2.0(m, 24H); 2.7–2.8(m, 1H); 2.85–2.95(m, 1H); 3.2–3.6(m, 4H); 3.9–4.1(m, 1H); 4.1–4.25(m, 1H); 4.74(q, 1H); 6.7–7.3(aromatic H, 4H) |

TABLE 1-continued

| Example No. | Formula | Data |
|---|---|---|
| A7 | (107) | 0.3–1.0(4t, 12H); 1.49(d, 3H); 1.5–2.25 (m, 8H); 2.7–2.8(m, 1H); 2.85–2.95(m, 1H); 3.3–3.4(m, 1H); 3.9–4.05(m, 1H); 4.1–4.25(m, 1H); 4.73(q, 1H); 6.75–7.35 (aromatic H, 8H) |
| A8 | (108) | Elemental Analysis:<br>calc. $C_{26}H_{43}NO_4$: 72.02% C, 9.99% H, 3.23% N.<br>found: 72.04% C, 9.87% H, 3.31% N. |
| A9 | (109) | Elemental Analysis:<br>calc. $C_{27}H_{35}NO_5$: 71.49% C, 7.78% H, 3.08% N.<br>found: 71.24% C, 7.92% H, 3.03% N. |
| A10 | (110) | $^1$H-NMR: (in ppm, 300 MHz)<br>0.5–1.8(m, 16H); 1.38(d, 3H); 2.67–2.70 (m, 1H); 2.81–2.85(m, 1H); 3.2–3.3(m, 1H); 3.9–4.2(m, 4H); 4.65(q, 1H); 6.79+ 7.15(aromatic H, 2x2H). m.p. 60.8–61.4° C. |
| A11 | (111) | m.p. 63–66° C. |

The examples given in table 2 are prepared analogously to example A4.

TABLE 2

| Example No. | Formula | Data |
|---|---|---|
| A12 | (112) | m.p. 44–46° C. |
| A13 | (113) | m.p. 90–92° C. |
| A14 | (114) | m.p. 72° C. |
| A15 | (115) | m.p. 81–82° C. |
| A16 | (116) | m.p. 43–47° C. |
| A17 | (117) | 0.5–2.0(m, 19H); 2.6(s, 3H); 3.6–3.75 (m, 1H); 4.5(s, 2H); 4.84(q, 1H); 7.2–7.5(aromatic H, 7H); 7.9–8.0(aromatic H, 2H); resin |

Table 3 gives further suitable compounds, which may be prepared in analogy.

TABLE 3
| Example No. | Formula |
| --- | --- |
| A18 | 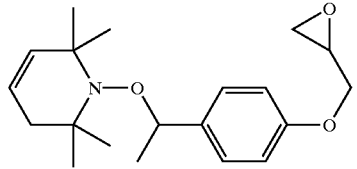 (118) |
| A19 | 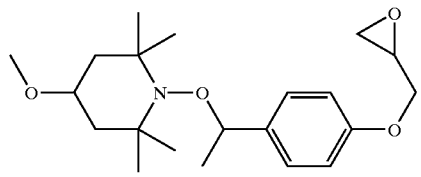 (119) |
| A20 | 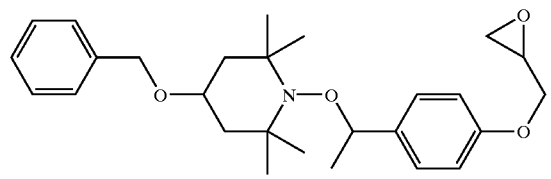 (120) |
| A21* | 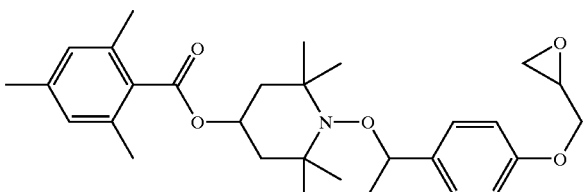 (121) |
| A22 | 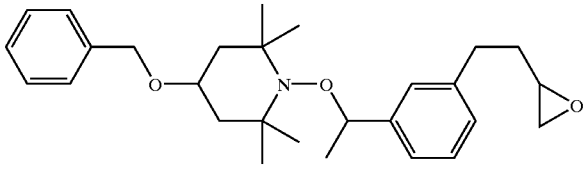 (122) |
| A23 | 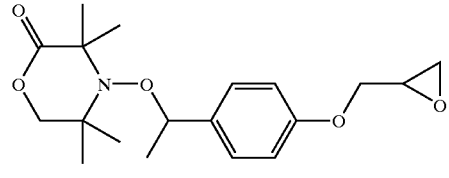 (123) |
| A24 | 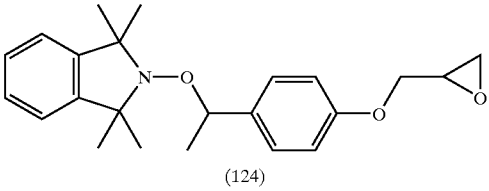 (124) |

TABLE 3-continued

| Example No. | Formula |
|---|---|
| A25 | 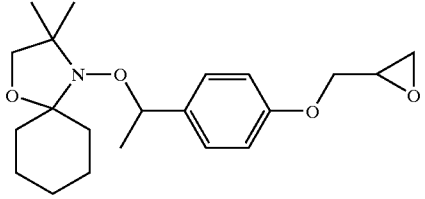 (125) |

B Polymerizations

Example B1

Styrene Polymerization

In a Schienk tube 2,2,6,6-tetramethyl-1-[1-(4-oxiranylmethoxy-phenyl)-ethoxy]-4-propoxy-piperidine (compound 101) are dissolved in 50 ml of distilled styrene. The solution is degassed according to the freeze and thaw technique and flushed with argon. After heating for 6 h in an oil bath to the temperature given in table 4 the excess monomer is removed in vacuum and the resulting white polymer is dried in a drying oven under vacuum. Weight average (Mw) and number average (Mn) molecular weights are determined using gel permeation chromatography (GPC). The results are given in Table 4

TABLE 4

| No. | Temp. (°C.) | Nitroxide (g, moles) | Conversion (%) | Mw | Mn | Mw/Mn |
|---|---|---|---|---|---|---|
| 1 | 120 | 0.170, 4.35 × 10$^{-4}$ | 36 | 45500 | 32800 | 1.39 |
| 2 | 120 | 0.392, 1.00 × 10$^{-3}$ | 16 | 13480 | 8620 | 1.56 |
| 3 | 130 | 0.170, 4.35 × 10$^{-4}$ | 52 | 59400 | 44100 | 1.32 |

What is claimed is:

1. A compound of formula (Ib)

(Ib)

wherein
the $R_2$ are independently $CH_3$ or $C_2H_5$;
A is a divalent group required to form a cyclic 5-or 6-membered ring and
$R_3$ is a radical of formula (II)

(II)

wherein
X is phenylene, naphthylene or biphenylene;

one $R_{12}$ is H and the other $R_{12}$ is $CH_3$;
D is a group or a group $C(O)$—$R_{13}$;
$R_{13}$ is $CH_3$ and
m is a number from 1 to 2.

2. A compound of formula (III) according to claim 1

(III)

wherein
$R_3$ has the meaning as defined in claim 1;
Y is H, $OR_{10}$, $NR_{10}R_{11}$, —O—C(O)—$R_{10}$ or $NR_{11}$—C(O)—$R_{10}$;
$R_{10}$ and $R_{11}$ independently are hydrogen, $C_1$–$C_{18}$alkyl, $C_2$–$C_{18}$alkenyl, $C_2$–$C_{18}$alkinyl or $C_2$–$C_{18}$alkyl which is substituted by at least one hydroxy group or, if Y is $NR_{10}R_{11}$, taken together, form a $C_2$–$C_{12}$alkylene bridge or a $C_2$–$C_{12}$-alkylene bridge interrupted by at least one O atom.

3. A compound according to claim 2, wherein $R_3$ is or

Y is H, $OR_{10}$ or $NR_{10}R_{11}$, —O—C(O)—$R_{10}$ or $NR_{11}$—C(O)—$R_{10}$;
$R_{10}$ and $R_{11}$ are independently hydrogen or $C_1$–$C_6$alkyl.

4. A polymerizable composition, comprising
a) at least one ethylenically unsaturated monomer or oligomer, and
b) an initiator compound of formula (Ib) according to claim 1.

5. A composition according to claim 4, wherein the ethylenically unsaturated monomer or oligomer is selected from the group consisting of styrene, substituted styrene, conjugated dienes, acrolein, vinyl acetate, (alkyl)acrylic acidanhydrides, (alkyl)acrylic acid salts, (alkyl)acrylic esters or (alkyl)acrylamides.

6. A composition according to claim 5 wherein the ethylenically unsaturated monomer is styrene, α-methyl styrene, p-methyl styrene or butadiene.

7. A composition according to claim 6, wherein the ethylenically unsaturated monomer is styrene.

8. A composition according to claim 4, wherein the initiator compound of formula (Ia) or (Ib) is preferably present in an amount of 0.01 mol-% to 10 mol-%, based on the monomer, oligomer or monomer/oligomer mixture used.

9. A process for preparing an oligomer, a cooligomer, a polymer or a copolymer (block or random) by free radical polymerization of at least one ethylenically unsaturated monomer/oligomer, which comprises (co)polymerizing the monomer or monomers/oligomers in the presence of an initiator compound of formula (Ib) according to claim 1 under reaction conditions capable of effecting scission of the O—R$_3$ (O—C) bond to form two free radicals, the radical .R$_3$ being capable of initiating polymerization.

10. A process according to claim 9, wherein the scission of the O—C bond is effected by heating, ultrasonic treatment or exposure to electromagnetic radiation, ranging from γ to microwaves.

11. A process according to claim 9, wherein the scission of the O—C bond is effected by heating and takes place at a temperature of between 50° C. and 180° C.

12. A process according to claim 9 for preparing a block copolymer involving at least two stages, which comprises forming a polymer with alkoxyamine end groups of the structure of formula (IVb)

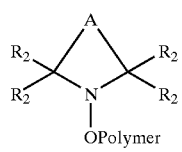

(IVb)

wherein
the R$_2$ are independently CH$_3$ or C$_2$H$_5$ and
A is a divalent group required to form a cyclic 5-or 6-membered ring and
R$_3$ is a radical of formula (II)

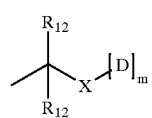

(II)

wherein

X is phenylene, naphthylene or biphenylene;
one R$_{12}$ is H and the other R$_{12}$ is CH$_3$;
D is a group

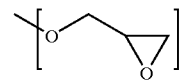

or a group C(O)—R$_{13}$;
R$_{13}$ is CH$_3$ and
m is a number from 1 to 2, the polymer containing the initiator group —R$_3$ and having the oxyamine group essentially attached as terminal group, and adding a further monomer followed by heating to form a block copolymer by radical initiated polymerization.

13. A polymer or oligomer, containing at least one initiator group —R$_3$ and at least one oxyamine group of formula

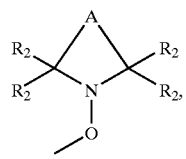

wherein the R$_2$ are independently CH$_3$ or C$_2$H$_5$;
A is a divalent group required to form a cyclic 5-or 6-membered ring and
R$_3$ is a radical of formula (II)

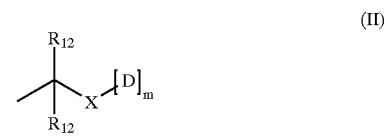

(II)

wherein
X is phenylene, naphthylene or biphenylene;
one R$_{12}$ is H and the other R$_{12}$ is CH$_3$;
D isa group

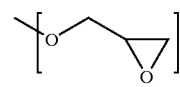

or a group C(O)—R$_{13}$;
R$_{13}$ is CH$_3$ and
m is a number from 1 to 2, obtained by the process according to claim 9.

* * * * *